United States Patent
Lee et al.

(10) Patent No.: US 6,906,204 B2
(45) Date of Patent: Jun. 14, 2005

(54) PROCESSING METHOD OF LACTIONIZATION IN THE PREPARATION OF STATINS

(75) Inventors: Kwang-hyeg Lee, Gyeonggi-do (KR); Jin-wan Kim, Seoul (KR); Kwang-do Choi, Gyeonggi-do (KR); Sang-ho Lee, Gyeonggi-do (KR); Hong-suk Cho, Gyeonggi-do (KR)

(73) Assignee: CJ Corp., Seoul (KR)

( * ) Notice: Subject to any disclaimer, the term of this patent is extended or adjusted under 35 U.S.C. 154(b) by 80 days.

(21) Appl. No.: 10/295,300

(22) Filed: Nov. 14, 2002

(65) Prior Publication Data

US 2003/0109723 A1 Jun. 12, 2003

(30) Foreign Application Priority Data

Dec. 3, 2001 (KR) ................. 10-2001-0075991

(51) Int. Cl.$^7$ ............................................. C07D 309/10
(52) U.S. Cl. ...................................................... 549/292
(58) Field of Search .......................................... 549/292

(56) References Cited

U.S. PATENT DOCUMENTS

| 5,939,564 A | 8/1999 | Kumar et al. |
| 6,294,680 B1 | 9/2001 | Vries et al. |
| 6,380,401 B1 | 4/2002 | McManus et al. |

*Primary Examiner*—Joseph K. McKane
*Assistant Examiner*—Rebecca Anderson
(74) *Attorney, Agent, or Firm*—Swanson & Bratschun, L.L.C.

(57) ABSTRACT

The present invention relates to a processing method for preparing lovastatin and simvastatin which comprises the steps of (1) performing lactonization of mevinic acid and its homologous compounds in the presence of a mixed organic solvent without an acid catalyst through nitrogen sweep; and (2) making crystals. In the process of the present invention, lovastatin and simvastatin highly purified can be produced in a high yield and especially, heterodimers formed as a by-product can be reduced remarkably. Therefore, the processing method of the present invention can be convenient and economical.

6 Claims, No Drawings

PROCESSING METHOD OF LACTIONIZATION IN THE PREPARATION OF STATINS

TECHNICAL FIELD

The present invention relates to a process for lactonizing mevinic acid or its homologous compounds. More particularly, the present invention relates to a process for preparing lovastatin and simvastatin in a high yield which comprises the steps of (1) performing lactonization of mevinic acid and its homologous compounds in the presence of mixed organic solvent without an acid catalyst through nitrogen sweep; (2) making crystals; and (3) separating lovastatin and simvastatin in a high purity.

BACKGROUND ART

Hypercholesterolemia is known as a major risk factor against ischemic heart disease such as arteriosclerosis. Bile acid sequestrants have been utilized to treat these diseases. However, this therapy seldom satisfies all the needs even if it seems effective. This drug should be administered in a large amount, namely several g doses per once.

Presently, lovastatin and its homologous compound, simvastatin are commercially available as highly active therapeutic agents for anti-hypercholesterolemia. They suppress HMG-CoA reductase, by which the cholesterol biosynthesis is inhibited. These compounds so-called statins are reported to exist in a dihydroxylic acid form with an open circular structure as depicted in formular 2 and in a lactone form as depicted in formular 1.

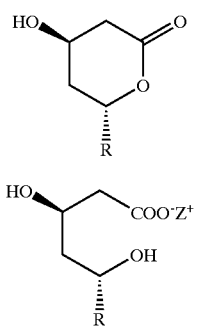

<Formular 1>

<Formular 2>

Wherein Z is hydrogen, ammonium or metal cation, R is a radical of formular 3 and $R_1$ is H or $CH_3$.

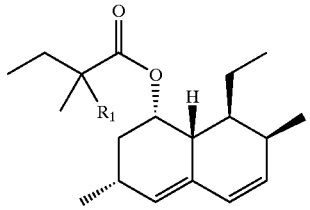

<Formular 3>

Statins are known to be active in a dihydroxylic acid form physiologically, but usually administered in a lactone form for patients. Therefore, it is necessary to develop an efficient method to perform a lactonization in a high productive yield. Since the lactonization is an equilibriated process, specific means should be utilized to transfer the equilibrium toward lactones as shown in reaction formular 1 in order to produce lactonized products in a high yield.

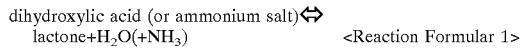

<Reaction Formular 1>

In U.S. Pat. No. 4,820,850, azeotropic distillation or nitrogen sweep were exploited to complete the lactonization by removing by-products of the reaction (water or ammonia) from reacted mixtures. However, there are several disadvantages. That is to say, it is generally refluxed under toluene solvent and should be heated at a high temperature (110° C.). Under such as high temperature, lactonized product cause inter-reaction between them, and results in increasing the amount of heterodimers as depicted in formula 1a.

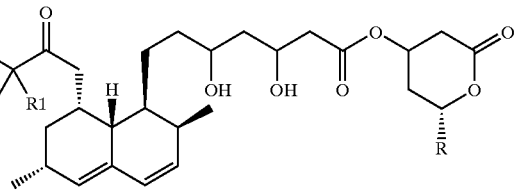

<Formular 1a>

Wherein, R and $R_1$ are defined as described above.

At this moment, the content of heterodimers reaches about 0.4% typically. This heterodimer is difficult to be purified from targeting lactone products, even if very precise recrystallization technique is applied. Practically, in case that these kinds of heterodimers are present, the total productive yield and the purity of lactone products are decreased. Therefore, the reaction mixture is diluted in a high degree before using in order to minimize the formation of heterodimers. However, this is also disadvantageous to the efficiency of the reaction.

Furthermore, Korean Patent Publication No. 97-11286 (U.S. Pat. No. 4,916,239) has disclosed another process for preparing lactones, in which the organic solvent mixed with water and having a solubility different enough between hydroxylate and lactone was utilized. Concretely, the separated hydroxylates of mevinic acid or its homologous compounds or the derivatives of ammonium salts or metal salts were reacted with one adopted among acetic acid, a mediator and strong acid catalysts and then an equilibrium between the separated hydroxylate and the lactone was formed. Afterward, water was added in a sufficient amount so as to crystallize the lactone completely. Unfortunately, in this method strong acids such as methanesulfonic acid, chloric acid, sulfuric acid, trifluoroacetic acid and the like should be utilized at the range of 1.2~1.5 M and strong bases also be added in a large amount to neutralize the solution. Therefore, this is not available for the industrial application in a large scale as well as very harmful environmentally. Besides, extra water should be blended in order to complete the lactonization, but this induces crystallization again onto the existing crystal, and become non-homogeneous. In addition, there are some other problems. The process might not be effective, since the resulting product be not filtrated thoroughly. Then, the procedure for the reaction and the work-up takes a very long time in the range of 9~12 hours, which reduces the productive yield. Furthermore, the resulting lactone product prepared by the above method still have heterodimers in less than 0.2%, typically in about 0.15%.

In order to improve the conventional method described above, U.S. Pat. No. 5,917,058 has illustrated the process for the preparing lactones, in which dihydroxy groups of statins or its homologous compounds, especially in an ammonium salt form, are reacted with acetic acid medium without an extra acidic catalyst and additional removing steps of water or ammonia, at 35~40° C. After that, insoluble solvent including water, hexane, cyclohexane or the like is added to produce lactones. However, in this method acetic acid as a solvent is utilized in 3~7-fold larger amounts than that of the reactant and should be neutralized with bases, and the neutral salt (ammonium acetate) is produced and remained in the final lactone compounds. Therefore, another process is required to recrystallize, which is inconvenient and uneconomical. The lactone compound and its neutral salts exist in a mixed state and are not filtrated properly, and the process for the preparation becomes inefficient. Furthermore, extra contaminant formed from the 3-hydroxy group of cyclolactone circle through dehydration can be observed in an acidic condition under a heated state, since only acetic acid is used as a solvent. This contaminant is not removed easily even by the recrystalization and might decrease the purity and the productive yield of lactone compounds.

Thus, U.S. Pat. No. 4,916,239 and No. 5,917,058 have disclosed that the lactonization be performed at a low temperature on account of organic or inorganic acid, however it is limited to reduce the heterodimers in the amount. Once the lactonization was accomplished, it is impossible to reduce heterodimer, since basically $H^+$ ion present in the reactant is reacted with the carbonyl group of lactone circle and makes heterodimers with other lactone products.

As demonstrated above, it is necessary to develop a new process for preparing lactone compounds in a high purity. Precisely, since lactone compounds are prepared in an equilibriated reaction from mevinic acid or its homologous compounds, the by-product (water and ammonia) might be removed from the reacted mixture so that the process for the preparation is completed. Through this procedure, the lactone compound is obtained in a high yield and the resulting heterodimers are reduced in the amount.

DISCLOSURE OF INVENTION

The inventors of the present invention have been studied in this field in order to overcome the foregoing and other disadvantages in the conventional methods described above. As a result, the inventors have developed a noble processing method for the lactonization in the preparation of statins so as to solve existed problems and completed the present invention successfully.

Therefore, the object of the present invention is to provide a process for preparing lactone compounds, which decreases the content of heterodimers remarkably as well as is convenient and economical.

The present invention relates to a processing method for lactonizing mevinic acid or its homologous compounds. More particularly, the present invention relates to a processing method for preparing compounds of formular 1 which comprises the steps of (1) performing lactonization of formular 2 in the presence of a mixed organic solvent without an acid catalyst through nitrogen sweep; and then (2) making lactone product in crystals.

<Formular 1>

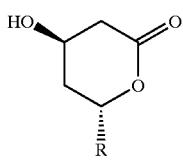

<Formular 2>

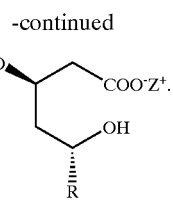

Wherein, Z is hydrogen, ammonium or metal cation, R is a radical as depicted in formular 3 and $R_1$ is H or $CH_3$.

<Formular 3>

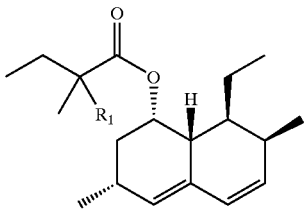

Particularly, the present invention provides the compound of formula 1, preferably 6(R)-[2-[8(s)-(2,2-dimethylbutyryloxy)-2(S),6(R)-dimethyl-1,2,6,7,8,8a(R)-hexahydronaphthyl]-1(S)ethyl]-4(R)-hydroxy-3,4,5,6-tetrahydro-2H-pyrane-2-on containing heterodimer contaminants in below 0.05%.

Hereinafter, the present invention will be illustrated more clearly.

In the present invention, the mixed organic solvent can be a mixture of more than two selected from a group comprising toluene, ethylacetate, isopropylacetate, dichloromethane, chloroform, tetrahydrofurane and acetone. Preferably, the mixed organic solvent can be a mixture of toluene and acetonitrile or of dichloromethane and acetonitrile. At this moment, the mixed organic solvent is preferable to be blended in 1:1 of volume ratio.

Concretely, the present invention using the mixed organic solvent can reduce the content of heterodimers of formula 1a which is produced from the esterification in between 3-hydroxy group of 3-hydroxylactone and separated acids remarkably as compared with the result of prior arts.

Preferably, the lactonization is performed under nitrogen sweep at a reflux temperature and more preferably, for about 3 hours.

The crystallizing solvent can be one or a mixture selected from a group comprising water, ethanol, isopropylalcohol, acetonitrile, acetone, dichloroethane, or chloroform. Preferably, the mixture can be a mixed solvent of ethanol and water or a mixed solvent of toluene and cyclohexane.

Preferably, the amount of the solvent for the crystallization can be a mixed solvent comprising 8~10 part by weight of water and 8~10 part by weight of ethanol, or a mixed solvent comprising 2~3 part by weight of toluene and 19~21 part by weight of cyclohexane against 1 part by weight of a dihydroxy, an ammonium salt form of statin and its homologous compounds. In the present invention, if the solvent amounts of water/ethanol and toluene/cyclohexane are more than this scope, the contaminants might not be removed easily as well as the crystallic property of solid disappears, which do not seem preferable.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of 6(R)-[2-[8(S)-(2,2-dimethylbutylyloxy)-2(S),6(R)-dimethyl-1,2,6,7,8,8a(R)-hexahydronaphthyl]-1(S)ethyl]-4(R)-hydroxy-3, 4,5,6-tetrahydro-2H-pyrane-2-on (simvastatin)

Ammonium 7-[1,2,6,7,8,8a(R)-hexahydro-2(S),6(R)-dimethyl-8(S)-(2,2,-dimethylbutylyloxy)-1(S)-naphthyl]-3(R),5(R)-dihydroxyheptanoate (2.42 g, 5.3 mmoles) was refluxed under nitrogen sweep at 80° C. for 3 hours in a mixture of toluene (50 ml) and acetonitrile (50 ml). The reaction mixture was cooled to 25° C. and 2.4 g of activated charcoal was added. Then, the reacted product was stirred for 30 minutes, filtrated and distilled under a decreased pressure for toluene so as to be adjusted to have 5 ml volume in the remained solution. This solution was blended with 50 ml of cyclohexane, and stirred for 3 hours. The crystals formed above was filtrated, washed using about 20 ml of toluene/cyclohexane (1:10 (v/v)) and dried under vacuum at 40° C. As a result, the compound 2.12 g (productive yield: 94.9%) of the present invention was obtained with 99% purity (HPLC). At this time, the amount of heterodimers reached 0.02%.

EXAMPLE 2

Preparation of 6(R)-[2-[8(S)-(2,2-dimethylbutylyloxy)-2(S),6(R)-dimethyl-1,2,6,7,8,8a(R)-hexahydronaphthyl]-1(S)ethyl]-4(R)-hydroxy-3, 4,5,6-tetrahydro-2H-pyrane-2-on (simvastatin)

Ammonium 7-[1,2,6,7,8,8a(R)-hexahydro-2(S),6(R)-dimethyl-8(S)-(2,2,-dimethylbutylyloxy)-1(S)-naphtyl]-3(R),5(R)-dihydroxyheptanoate (2.42 g, 5.3 mmoles) was refluxed under nitrogen sweep at 80° C. for 3 hours with a mixture of dichloroethane (50 ml) and acetonitrile (50 ml). The reaction mixture was cooled to 25° C. and 2.4 g of activated charcoal was added. Then, the reacted product was stirred for 30 minutes, filtrated and distilled under a decreased pressure. Afterward, 21.2 ml of ethanol was added to the remaining solution and heated to 40° C. Then, 21.2 ml of water was blended properly and stirred for 30 minutes. In case that crystal was made, the resulting solution was cooled to 4° C. and stirred for 2 hours. The crystal formed above was filtrated, washed using about 20 ml of the mixed solvent in water/ethanol (1:1 (v/v)) at 4° C. and then dried under vacuum at 40° C. As a result, the compound 1.97 g (productive yield: 88.2%) of the present invention was obtained with 99% purity (HPLC). At this time, the amount of heterodimers reached 0.02%.

EXAMPLE 3

Preparation of 6(R)-[2-[8(S)-(2-methylbutylyloxy)-2(S),6(R)-dimethyl-1,2,6,7,8,8a(R)-hexahydronaphthyl]-1(S)ethyl]-4(R)-hydroxy-3,4,5, 6-tetrahydro-2H-pyrane-2-on (lovastatin)

Ammonium 7-[1,2,6,7,8,8a(R)-hexahydro-2(S),6(R)-dimethyl-8(S)-(2-methylbutylyloxy)-1(S)-naphthyl]-3(R),5(R)-dihydroxyheptanoate (2.42 g, 5.5 mmole) was utilized as a starting material. Then, the other procedure was performed as described in Example 1 so as to prepare the compound of the present invention. As a result, the compound 2.1 g (productive yield: 93.0%) of the present invention was obtained with 99.0% purity (HPLC). At this time, the amount of heterodimers reached 0.01%.

EXAMPLE 4

Preparation of 6(R)-[2-[8(S)-(2-methylbutylyloxy)-2(S),6(R)-dimethyl-1,2,6,7,8,8a(R)-hexahydronaphtyl]-1(S)ethyl]-4(R)-hydroxy-3,4,5,6-tetra hydro-2H-pyrane-2-on (lovastatin)

Ammonium 7-[1,2,6,7,8,8a(R)-hexahydro-2(S),6(R)-dimethyl-8(S)-(2-methylbutylyloxy)-1(S)-naphtyl]-3(R),5 (R)-dihydroxyheptanoate (2.42 g, 5.5 mmole) was utilized as a starting material. Then, the other procedure was performed as described in Example 2 so as to prepare the compound of the present invention. As a result, the compound 2.1 g (productive yield: 93.5%) of the present invention was obtained with 99.1% purity (HPLC). At this time, the amount of heterodimers reached 0.02%.

INDUSTRIAL APPLICABILITY

In accordance with the present invention, lovastatin and simvastatin in a highly purified state can be produced in a highly productive yield and especially, and the amount of heterodimers as a by-product can be reduced remarkably to below 0.5% and commonly below 0.02% as well as the whole procedure might be convenient and economical.

Those skilled in the art will also appreciate that such equivalent embodiments do not depart from the spirit and scope of the invention as set forth in the appended claims.

What is claimed is:

1. A processing method for preparing a compound of formula 1 which comprises the steps of (1) performing lactonization of a compound of formula 2 in the presence of a mixed organic solvent without a catalyst through nitrogen sweep; and (2) making lactone product into crystal;

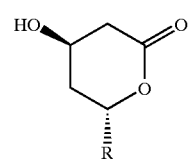

<Formula 1>

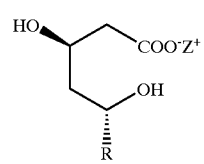

<Formula 2> wherein Z is hydrogen, ammonium or metal cation, R is a radical of formular 3 and $R_1$ is H or $CH_3$.

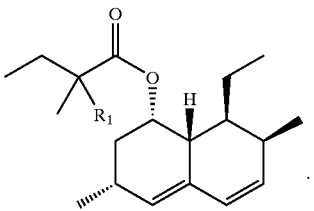

<Formula 3>

2. The processing method for preparing the compound according to claim 1, wherein said mixed organic solvent can be a mixture of more than two selected from a group consisting of toluene, ethyl acetate, isopropyl acetate, dichloromethane, chloroform, tetrahydrofuran and acetone.

3. The processing method for preparing the compound according to claim 1, wherein said mixed organic solvent is a mixture of toluene and acetonitrile, or dichloromethane and acetonitrile.

4. The processing method for preparing the compound according to any one of claims 1 to 3, wherein said mixed organic solvent is utilized in 40 part by weight against 1 part by weight of the compound of formula 2.

5. The processing method for preparing the compound according to claim 1, wherein said step of making lactone product into crystal utilize more than one solvent selected from a group consisting of water, ethanol, isopropyl alcohol, n-hexane, cyclohexane, toluene, ethyl acetate, isopropyl acetate, acetonitrile, acetone, dichloroethane and chloroform.

6. The processing method for preparing the compound according to claim 5, wherein said solvent is a mixed solvent comprising 8 to 10 part by weight of water and 8 to 10 part by weight of ethanol, or a mixed solvent comprising 2 to 3 part by weight of toluene and 19 to 21 part by weight of cyclohexane against 1 part by weight of the compound of formula 2.

* * * * *